United States Patent [19]

Farr

[11] 4,450,079

[45] May 22, 1984

[54] CASSETTE FOR PROVIDING A CONTROLLED FLOW OF FLUID

[75] Inventor: Andrew F. Farr, Spring Valley, Calif.

[73] Assignee: IMED Corporation, San Diego, Calif.

[21] Appl. No.: 320,192

[22] Filed: Nov. 12, 1981

Related U.S. Application Data

[63] Continuation of Ser. No. 073,097, Sep. 6, 1979, abandoned.

[51] Int. Cl.³ .............................................. A61M 5/00
[52] U.S. Cl. ..................................... 604/152; 604/230
[58] Field of Search .............. 92/158, 159; 128/214 F, 128/214 E; 604/152, 230

[56] References Cited

U.S. PATENT DOCUMENTS 3,055,720  9/1962  Price ..................................... 309/51
3,985,133 10/1976  Jenkins et al. ................... 128/214 F

FOREIGN PATENT DOCUMENTS 82242  9/1917  Austria ................................. 92/159

*Primary Examiner*—Frank A. Spear, Jr.
*Attorney, Agent, or Firm*—Ellsworth R. Roston; Charles H. Schwartz

[57] ABSTRACT

Apparatus is provided for obtaining a controlled flow of fluid from a source to a patient. The apparatus includes a plunger movable vertically in a chamber and made from resilient material and having a pair of vertically spaced lands. The chamber defines a recess with the lands and the plunger in the space between the lands. Lubricating fluid is disposed in the recess. Fluid such as intravenous fluid is introduced into the chamber in one reciprocal movement of the plunger and is withdrawn from the chamber in the other reciprocal movement of the plunger. A porous washer filled with lubricating fluid is disposed in contiguous relationship to a particular one of the lands for providing an auxiliary reservoir of the lubricating fluid. Such washer may be contiguous to the lower one of the two (2) lands. The auxiliary reservoir may be yieldable and may be provided with an external dimension greater than the external dimension of the lands to facilitate a wiping action with the chamber during the vertical movement of the plunger in the chamber. Lubricating fluid passes upwardly from the washer into the recess during the upward movement of the plunger.

20 Claims, 3 Drawing Figures

U.S. Patent    May 22, 1984    4,450,079
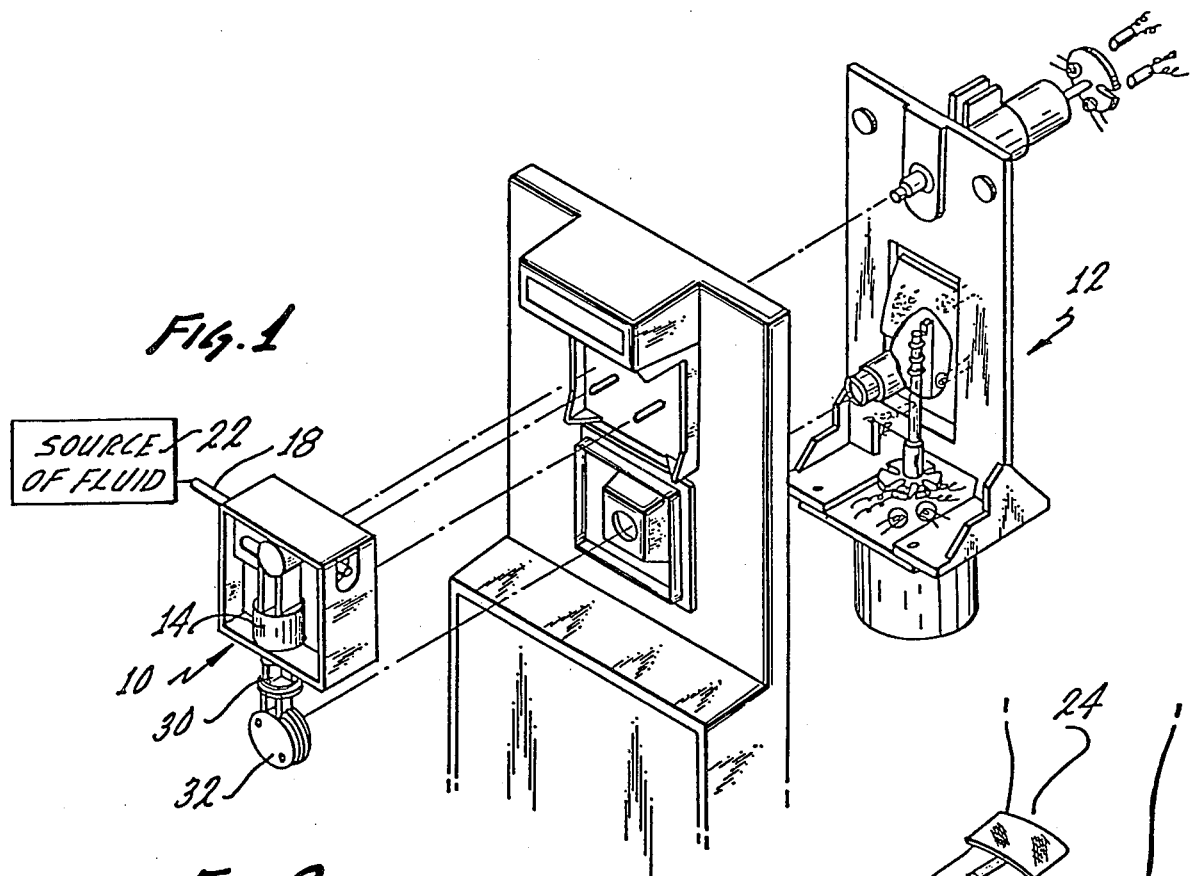
Fig. 1
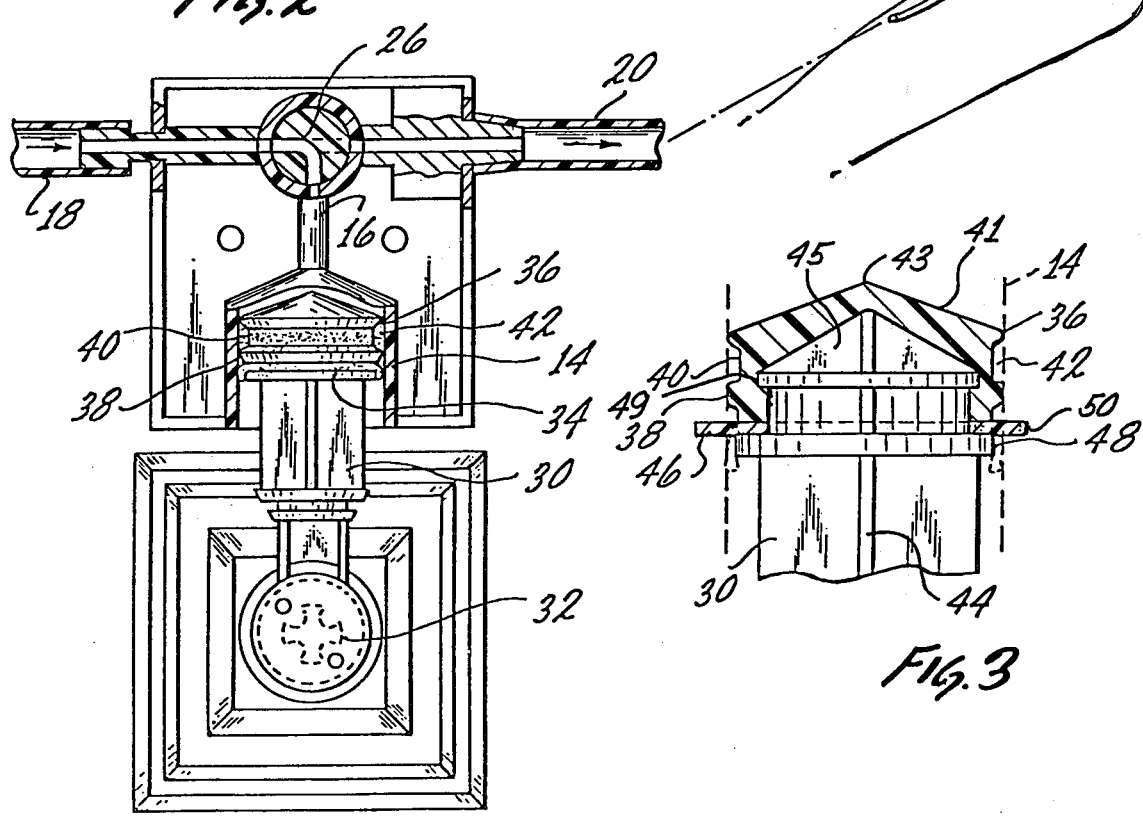
Fig. 2
Fig. 3

CASSETTE FOR PROVIDING A CONTROLLED FLOW OF FLUID

This is a continuation of application Ser. No. 073,097, filed Sept. 6, 1979, now abandoned.

This invention relates to apparatus for providing a controlled flow of fluid from a source to a patient. More particularly, the invention relates to apparatus for providing a transfer of precise amounts of fluid from a source to a patient at preselected rates over extended periods of time.

BACKGROUND OF THE INVENTION

As human knowledge has advanced, medical treatment has become progressively sophisticated. For example, it has become increasingly apparent to medical technicians that a patient has to receive intravenous fluid in precise amounts at preselected rates over extended periods of time. If the patient receives the fluid at a reduced rate, his ability to recover is impeded. However, if the patient receives fluid at a rate greater than the preselected value, he can often become poisoned by the chemicals in the fluid.

Systems have been provided in recent years for introducing controlled amounts of fluid to a patient at a preselected rate. For example, such a system is disclosed and claimed in U.S. Pat. No. 3,985,133 issued to Jon J. Jenkins et al on Oct. 12, 1976 for an "IV Pump" and assigned of record to the assignee of record of this application. A cassette is included in such a system. The cassette is provided with a chamber having a substantially constant cross section and is also provided with a plunger reciprocable in opposite directions in the chamber. The displacement and the rate of displacement of the plunger are precisely controlled by the system to provide for the introduction of the fluid to the patient at the preselected rate.

In the system disclosed and claimed in U.S. Pat. No. 3,985,133, the plunger has been provided with a pair of spaced lands and with a recess between the lands. Lubricating fluid has been provided between the recesses to lubricate the plunger as the plunger has been reciprocated. By lubricating the plunger, a continued and efficient reciprocatory movement of the plunger has been assured in most instances. However, the recess has occasionally become dry after some reciprocatory movement of the plunger. This has sometimes caused the plunger to become stuck in the chamber. The sticking has been aggravated by an expansion of the lands as a result of a generation of heat as the lands have moved through the chamber without any lubrication. This has caused the pump to become occluded and has prevented intravenous fluid from being transferred properly to a patient.

SUMMARY OF THE INVENTION

This invention provides improvements in a cassette for assuring a proper transfer of intravenous fluid to a patient. The invention includes a chamber having a substantially constant cross section and also includes plunger reciprocable in the chamber in a particular direction. The plunger may be made from a resilient material and may be provided with a pair of lands spaced from each other in the particular direction. The chamber defines a recess with the lands and the plunger in the space between the lands. A lubricating fluid is disposed in the recess to provide a lubricating action.

Means are operatively coupled to the plunger for providing a reciprocation of the plunger in the chamber. Fluid such as intravenous fluid is introduced into the chamber in one reciprocal movement of the plunger means and is withdrawn from the chamber in the other reciprocal movement of the plunger means. One of the lands is disposed contiguous to the intravenous fluid stored in the chamber and the other land is displaced from the intravenous fluid stored in the chamber.

Means are movable with the plunger and are disposed in contiguous relationship to a particular one of the lands for providing an auxiliary reservoir of the lubricating fluid. Such auxiliary reservoir means may be contiguous to the land displaced from the fluid in the chamber. Such means may be porous and the lubricating fluid may be disposed in the pores. The auxiliary reservoir means may be yieldable and may be provided with an external dimension greater than the external dimension of the lands to facilitate the wiping action between such means and the chamber. The auxiliary reservoir means may be in the form of a relatively thin porous washer made from a suitable material such as polyurethane.

BRIEF DESCRIPTION OF THE DRAWINGS

In the drawings:

FIG. 1 is an exploded perspective view on a schematic basis of a pump and a cassette operative with the pump to provide for the introduction of fluid to a patient;

FIG. 2 is an enlarged sectional view of the cassette shown in FIG. 1; and

FIG. 3 is a still further enlarged sectional view of a plunger included in the cassette.

DETAILED DESCRIPTION OF THE INVENTION

In one embodiment of the invention a cassette generally indicated at 10 is adapted to be used in volumetric pump generally indicated at 12. The volumetric pump 12 may be constructed in a manner similar to that disclosed and claimed in U.S. Pat. No. 3,985,133 issued to Jon J. Jenkins et al. However, it will be appreciated that other pumps may be used and that, actually, any equipment capable of transferring fluid from a source to a patient may be used. It will also be appreciated that other cassettes may be used than that disclosed and claimed in U.S. Pat. No. 3,985,133.

The cassette 10 is disposable. Thus, after use in transferring fluid from a source to a patient, the cassette may be discarded and a different cassette may be substituted. This eliminates any need for sterilizing the cassette after each use. Furthermore, the cassette is operatively disposed relative to the pump so that the fluid flows only through the cassette and does not flow through the pump. This allows for the replacement of different cassettes in the pump without requiring that the pump be sterilized.

The cassette 10 includes a chamber 14 made from a suitable material such as a glass or a plastic material, preferably translucent. The chamber 14 is provided with a substantially constant cross-sectional area along its axial length and is preferably cylindrical. A conduit 16 is provided at one end of the pump. The conduit 16 branches at one end into a pair of lines 18 and 20. The line 18 extends from a source 22 and the line 20 extends to a patient 24. A rotatable two-position valve 26 is included in the conduit and is operative in one position to provide for a passage of fluid such as intravenous fluid from the source 22 to the chamber and is operative in the second position to provide for a transfer of fluid from the chamber 14 to the patient. The valve 26 is operative by the pump 12.

A piston 30 is disposed in the chamber 14 and is movable axially in the chamber. The piston 30 is provided with a detent 32 which mates with a corresponding detent in the pump to provide for the reciprocal movement by the pump of the piston 30. A plunger 34 is disposed at the end of the piston 30 adjacent the conduit 16 and may be made from a suitably resilient material such as a butyl rubber. The plunger 34 is provided with a side wall having a pair of lands 36 and 38 spaced from each other in the axial direction and defining a recess 40 with the chamber 14. A suitable lubricating fluid 42 such as a silicone oil may be disposed in the recess. The silicone oil 42 may be a Dow 360 type and may have a volume of approximately twenty-five (25) to one hundred and fifty (150) microliters in the recess 40.

The plunger 34 is provided with a cap 41 at a position above the lands 36 and 38, the cap being domed to define a peak 43. A pusher member 44 is provided with a brace portion 45 at its upper end. The brace portion 45 is defined by four (4) braces disposed in a quadrant arrangement relative to one another. The braces of the brace portion 45 abut the inner surface of the cap 41 at its upper end and extend to the peak 43. A support member 47 is supported by the pusher member 44 at a position near the upper end of the pusher member and is disposed transversely to extend into a socket 49 in the plunger 34 at a position between the lands 36 and 38 in the axial direction.

A washer 46 made from a suitably yieldable material such as a polyurethane foam is disposed on a collar 48 on the piston 30 at a position adjacent the land 38. The washer 46 is porous and the pores are filled with a lubricating fluid 50 preferably corresponding to the lubricating fluid 42. The washer 46 may be provided with external dimensions greater than the external dimensions of the lands 36 and 38 so that the washer will wipe against the surface of the chamber 14 during the reciprocatory movements of the piston 30. In effect, the washer 46 serves as an auxiliary reservoir for the lubricating fluid.

The volumetric pump 10 includes a stepper motor (not shown) which operates to step the plunger 34 through successive increments, all having an equal distance. While the plunger is being withdrawn in the successive increments from the conduit 16, a vacuum is produced in the chamber 14 for introducing the intravenous fluid from the source 22 into the chamber. During the time that the plunger is being moved in the successive increments toward the conduit 16, the intravenous fluid is transferred from the chamber 14 to the patient.

While the plunger 34 is being stepped toward the conduit, the land 36 is being lubricated by the fluid 42 in the recess 40 and also by intravenous fluid in the chamber. However, the land 36 tends to wipe the wall of the chamber 14 and remove any lubrication during the movement of the plunger 34 toward the conduit 16. The land 38 is also lubricated by the fluid in the recess 40 during such movement of the plunger 34.

During the movement of the plunger 34 away from the conduit 16, the land 38 is at the leading end of the plunger. The land 38 tends to be lubricated by the fluid 42 in the recess 40 during such movement of the plunger. The land 36 also tends to be lubricated by the fluid 42 in the recess 40 during such movement of the plunger.

As will be seen from the above discussion, the lands 36 and 38 tend to become lubricated by the fluid 42 in the recess 40 during the reciprocatory movements of the plunger 34. Although there is only a limited amount of fluid 42 in the recess 40, this amount of fluid has been found sufficient in most instances to maintain lubrication of the lands 36 and 38 even for the maximum period of time that the cassette 12 may be used before it is discarded.

It has sometimes happened that the fluid 42 in the recess 40 has become depleted before the use of a cassette has been completed. This has sometimes presented problems. For example, during the movement of the plunger 34 toward the conduit 16, the intravenous fluid in the chamber 14 tends to lubricate the land 36. However, the land 36 tends to wipe this fluid. The wiping action is completed by the land 38, which is separated from the land 36 by a dry area. As a result, the land 38 receives no lubrication during its movement in a direction away from the conduit 16. This tends to cause the land 38 to become stuck against the chamber 14 during its movement away from the conduit 16. The sticking tends to become aggravated by swelling of the land 38 against the chamber as a result of a generation of heat as the land 38 moves along the chamber without any lubrication. As a result, the pump becomes occluded.

The washer 46 is instrumental in increasing the reciprocatory life of the plunger 34. It leads the lands 36 and 38 during the movement of the plunger away from the conduit 16 and wipes against the chamber 14 during such movement. This brushing action causes the chamber 14 to become lubricated in advance of the movement of the lands 36 and 38 and prevents the land 38 from being stuck against the chamber. The yielding nature of the washer 46 and the overside construction of the washer facilitate the lubricating action of the washer. In this way, the operating life of the cassette 12 is considerably enhanced. Actually, by including the washer 46 as an auxiliary reservoir of lubricating fluid, the amount of fluid in the recess 40 can be reduced and the operating life of the cassette 12 can still be maintained within desirable limits.

Although this application has been disclosed and illustrated with reference to particular applications, the principles involved are susceptible of numerous other applications which will be apparent to persons skilled in the art. The invention is, therefore, to be limited only as indicated by the scope of the appended claims.

I claim:

1. In combination in a vertically disposed cassette for providing a controlled flow of fluid between a source and a patient, a chamber having a wall defining a substantially constant cross sectional area, a piston member disposed in the chamber and reciprocable in a first substantially downward direction for receiving the fluid into the chamber and reciprocable in an opposite substantially upward direction for transferring fluid from the chamber, plunger means at the end of the piston member and including a recessed wall and a land at the end of the recessed wall for engaging the chamber during the reciprocation of the piston member in the upward and downward directions, the land being disposed at the leading end of the recess in the movement of the plunger means in the downward direction, there being a lubricating fluid in the space between the recessed wall and the wall of the chamber, and a porous washer member supported on the piston member at a position below the land and at a position slightly displaced from the bottom end of the land, there being a lubricating fluid in the pores of the washer member for facilitating the flow of the lubricating fluid into the space between the recessed wall and the wall of the chamber during the upward movement of the washer member.

2. In the combination set forth in claim 1, the porous washer member being provided with greater external dimensions than the land in the plunger means and being provided with properties of yielding during the reciprocatory movements of the piston member.

3. The combination set forth in claim 2 wherein the washer member is made from a polyurethane having porous properties and the lubricating fluid is a silicone oil.

4. The combination set forth in claim 3 wherein the plunger means is a butyl rubber.

5. The combination set forth in claim 2, including, the piston member being provided with a pusher member extending upwardly through the piston member and being further provided with a support member supported by the pusher member and extending laterally from the pusher member, the plunger means being formed by a hollow member defining at its inner surface a socket for receiving the periphery of the support member at a position vertically between the lands.

6. The combination set forth in claim 5, including, the plunger means being provided with a cap at its upper end, the cap being domed to define a vertical peak in the cap, the pusher member extending through the piston to a position abutting the cap at the vertical peak in the domed cap.

7. The combination set forth in claim 5, including, a collar disposed relative to the washer member to limit any movement of the washer member downwardly from the recess during the upward movement of the plunger means.

8. In combination in apparatus for providing a controlled flow of fluid from a source to a patient, plunger means reciprocal upwardly and downwardly and made from a resilient material and having a pair of lands spaced vertically from each other, a chamber receiving the plunger means for upward and downward reciprocation of the plunger means and defining a recess with the lands and the plunger means in the space between the lands, lubricating means disposed in the recess to provide a lubricating action during the reciprocatory movement of the plunger means, means operatively coupled to the plunger means for providing for an upward and downward reciprocation of the plunger means in the chamber to obtain an introduction of the fluid into the chamber in the downward movement of the plunger means and to obtain a withdrawal of the fluid from the chamber in the upward movement of the plunger means, and means operatively coupled to the reciprocating means and movable with the reciprocating means and disposed below the lower one of the lands at a position near the bottom end of the recess for providing an auxiliary reservoir of the lubricating fluid to obtain a transfer of the lubricating fluid from the auxiliary reservoir into the recess during the upward movement of the reciprocating means.

9. The combination set forth in claim 8 wherein the means providing the auxiliary reservoir is displaced downwardly from the recess and is porous and lubricating fluid is stored within the pores.

10. The combination set forth in claim 9 wherein a collar is disposed on the plunger means below the auxiliary reservoir means and auxiliary reservoir means is disposed on the collar.

11. The combination set forth in claim 10 wherein the lands have a first lateral dimension and the auxiliary reservoir means has a second lateral dimension greater than the first lateral dimension and is made from a yieldable material.

12. The combination set forth in claim 11, including, a domed peak on the plunger means at the upper vertical extremity of the plunger means, and a pusher member extending through the plunger means and abutting the plunger means at the domed peak.

13. The combination set forth in claim 12 wherein the plunger means is provided with a socket at a position vertically between the lands, a support member extends laterally from the pusher member into the socket in the plunger means, and the collar is disposed relative to the washer member to limit any movement of the washer member from the recess during the upward movement of the plunger means.

14. In combination for use in a cassette having a chamber for storing intravenous fluid and having a piston reciprocable vertically in the chamber for transferring fluid into the chamber during movement of the piston downwardly in the chamber and for transferring fluid from the chamber during movement of the piston upwardly in the chamber, a plunger provided with a closed configuration including a side wall and a pair of lands extending laterally outwardly from the sidewall at spaced positions in the vertical direction along the length of the sidewall to define a recess with the sidewall between the lands, washer means disposed below the plunger and movable with the plunger and provided with porous characteristics for storing lubricating fluid and disposed near a particular one of the lands for leading the lands during the downward movement of the plunger and for trailing the lands in the upward movement of the plunger, and lubricating fluid disposed in the pores of the washer means for transfer into the recess during the upward movement of the plunger.

15. The combination set forth in claim 14 wherein the washer means is provided with lateral dimensions greater than the lateral dimensions of the lands.

16. The combination set forth in claim 15 wherein the washer means is made from a yieldable material and the plunger is made from a resilient material and is provided with a collar displaced downwardly from the lands and the washer means is disposed on the collar.

17. The combination set forth in claim 16 wherein the washer means is a porous polyurethane and the plunger is made from a butyl rubber.

18. The combination set forth in claim 16 wherein the washer means is disposed on the upper end of the collar.

19. The combination recited in claim 18, including, the plunger being provided with a socket at a position vertically between the lands,
a pusher member extending vertically through the plunger and a support member extending laterally from the pusher member into the socket in the plunger.

20. The combination recited in claim 19, including, the plunger being provided with a domed peak at its uppermost position and the pusher member abutting the plunger at the position of the domed peak.

* * * * *